United States Patent [19]
Keep et al.

[11] Patent Number: 5,972,924
[45] Date of Patent: Oct. 26, 1999

[54] TREATMENT OF CEREBRAL ISCHEMIA AND CEREBRAL DAMAGE WITH NEUROPROTECTIVE AGENTS

[75] Inventors: Marcus Floyd Keep, Honolulu, Hi.; Eskil Mats Elmér; Merab Kokaia, both of Lund, Sweden; Hiroyuki Uchino, Tokyo, Japan; Zaal Kokaia; Hakan Widner, both of Lund, Sweden; Qi Zhao, Sunnyvale, Calif.; Keiko Uchino, Tokyo, Japan

[73] Assignee: Maas BiolAB, LLC, Honolulu, Hi.

[21] Appl. No.: 08/860,898

[22] PCT Filed: Jan. 18, 1996

[86] PCT No.: PCT/SE96/00036

§ 371 Date: Jul. 11, 1997

§ 102(e) Date: Jul. 11, 1997

[87] PCT Pub. No.: WO96/22104

PCT Pub. Date: Jul. 25, 1996

[30] Foreign Application Priority Data

Jan. 20, 1995 [SE] Sweden .................. 9500209

[51] Int. Cl.[6] .................................................. A61K 31/33
[52] U.S. Cl. ............................................................. 514/183
[58] Field of Search ............................................. 514/183

[56] References Cited

U.S. PATENT DOCUMENTS 4,117,118  9/1978  Härri et al. ............................ 424/177

OTHER PUBLICATIONS

Shiga et al., Chemical Abstracts (118: 93972) Cyclosporin A protects against ischemia–reperfusion injury in the brain.

*Primary Examiner*—Kevin E. Weddington

[57] ABSTRACT

The invention provides pharmaceutical compositions and medications useful for the treatment of cerebral ischernia, cerebral insult, and cerebral disorders using the active treatment medication cyclosporin A, variants or pharmaceutically acceptable derivatives thereof, inconditions, situations and methods wherein the blood-brain barrier has been opened, disrupted, bypassed, transgressed, obviated or crossed,such that cyclosporin A, variants or pharmaceutically acceptable derivatives thereof come into contact with neurons and neuron support cells. Included in the invention are methods for the use of the said pharmaceutical compositions and medications. Also included in the invention are conditions, situations and methods whereby the active treatment medication can come in contact with neurons and neuron support cells.

16 Claims, No Drawings

TREATMENT OF CEREBRAL ISCHEMIA AND CEREBRAL DAMAGE WITH NEUROPROTECTIVE AGENTS

This application is a 371 of PCT/SE96/00036 filed Jan. 18, 1996.

Central nervous tissue & to a lesser extent, peripheral nervous tissue, has poor reparative abilities. Thus damage to nervous tissue causes significant permanent disability & is a frequent cause of death. Damage to nervous tissue occurs in many ways, including ischemia in cerebrovascular accidents, cerebral circulatory disturbances, episodes of absolute & relative hypoxia, from metabolic disturbances, & from various forms of trauma. In areas of focal ischemia or damage, there is a core of more profound damage, surrounded by a perifocal penumbra of lesser damage. The neurons in the penumbra can for a time maintain homeostasis, & are potentially more salvageable by pharmacological agents.

Current treatment of nervous damage is limited. Supportive measures are taken in hospital during the period after nervous insult, such as stroke or trauma. Several medications have met with differing but incomplete success as agents to protect nervous function from insult. Nimodipine, a calcium channel blocker, is used clinically to treat vasospasm after subararchnoid hemorrhage. Methyaprednisolone, a steroid, in very high doses is helpful in spinal cord compression. Tirilazad, a 21-aminosteroid linked to a free radical scavenger, is undergoing clinical trials to decrease the damage caused by stroke. The high rate of disability from nervous insult, & current lack of a truely effective neuroprotective agent demonstrates the need for such a discovery.

It has now been discovered that the treatment medication known as cyclosporin A having the formula:

is a useful & effective neuroprotective agent.

It is already known that cyclosporin A is an immunosuppressive drug. The above mentioned treatment medication has already been described, in U.S. Pat. No. 4,117,118 & numerous patents since, which relate to its production, formulation & immunosuppressive properties.

Cyclosporin A is a product of the fungus Tolypocladium Inflatum Gams. It is a cyclic poly-amino acid molecule, consisting of 11 amino acids. One of the amino acids is unique for cyclosporin A, a β-hydroxyamino acid called butenyl-methyl-threonin (MeBmt). The molecular weight is 1202.6 & the chemical composition is $C_{62}H_{111}N_{11}O_{12}$.

The molecule is highly lipophilic, & virtually insoluble in water. The bioavailability after an oral dose varies between 8 & 60% depending in part on the bile flow. The drug is absorbed mainly in the small intestine. The drug is transported in the blood within red blood cells to about 58%, & the remaining approximately 10–20% in leukocytes, & 33% bound to plasma proteins. In the plasma cyclosporin A is bound to high-density lipoproteins & low-density lipoproteins & very-low density lipoproteins, & a small fraction to albumin. A very small fraction is free in the plasma.

The drug undergoes extensive metabolism, mainly in the liver by the cytochrome P450 system. There are at least 30 known metabolites of cyclosporin A, with various chemical modifications, such as hydroxylation, demethylation, oxidation & epoxide formations. There are a number of variants of cyclosporin A, differing for example in one amino acid, which have similar pharmacological properties.

There is an enterohepatic circulation, & gut bacteria can metabolize the drug, with a further uptake of the metabolites in patients. 95% of a single dose given orally can be found in the feces within 95 hrs. The remaining fraction is excreted via the kidneys. Under normal conditions cyclosporin A & its metabolites do not pass the blood-brain barrier.

This entire family of cyclosporins, all derivatives, variants, amino acid variants, metabolites, including variations of mono-, di- & trihydroxylates, N-demethylates, aldehydes, carboxylates, conjugates, sulfates, glucuronides, intramolecular cyclizations & those without a cyclic structure as well as shorter peptides & amino acids & their derivatives & salts will hereinafter be referred to as cyclosporins. Pharmacologically acceptable forms of cyclosporins will hereinafter be referred to as treatment medication or treatment medications.

The present invention also discloses treatment medications of the family of cyclosporins & all known salts, variants, amino acid variants, derivatives, metabolites & their salts & derivatives for use in treatments of the conditions listed below, as well as the use of such treatment medications for the treatment of such conditions. This includes cyclosporin A, cyclosporin C, cyclosporin D, cyclosporin G. This includes all products of the fungus Tolypocladium Inflatum Gams. Some known metabolites of cyclosporin A include the following: (according to Hawk's Cay nomenclature) AM1, AM9, AM1c, AM4N, AM19, AM1c9, AM1c4N9, AM1A, AM1A4N, AM1Ac, AM1AL, AM11d, AM69, AM4N9, AM14N, AM14N9, AM4N69, AM99N, Dihydro-CsA M17, AM1c-GLC, sulfate conjugate of cyclosporin, unfdl, BH11a, BH15a, B, G, E, (and with come overlap with the Hawk's above, according to Maurer's nomenclature) M1, M2, M3, M4, M5, M6, M7, M8, M9, M10, M11, M12, M13, M14, M15, M16, M17, M18, M19, M20, M21, M22, M23, M24, M25, M26, MUNDF1 & MeBMT. Some metabolites of cyclosporin G include GM1, GM9, GM4N, GM1c, GM1c9, & GM19.

The nervous system compromises many structures, which includes the following components. These components are neurons, neural support cells, glia, Schwann cells, vasculature contained within & supplying these structures, the central nervous system, the brain, the brain stem, the spinal cord, the junction of the central nervous system with the peripheral nervous system, the peripheral nervous system, & allied structures all of which are defined herein as nervous tissue.

Function of the nervous system & its parts, are manifest in sensing the environment, awareness of it, homeostasis to it & interaction with it. Function of the nervous system is manifest, by example, in the ability to perform activities of daily living, work, cogitation, & speech. These functions of the nervous tissue are defined herein as nervous function.

Damage to nervous tissue can occur in many ways & come from many sources, with many different sequelae, which includes the following. Damage to nervous tissue & death of nervous tissue, brain damage & brain destruction, in whole or part, & resultant morbidity, disability, neurologic deficit & death are defined herein as nervous insult.

Nervous insult can be from various origins including ischemia, hypoxia, cerebrovascular accident, metabolic, toxic, neurotoxic, trauma, surgery, iatrogenic, pressure, mass effect, hemorrhage, thermal, chemical, radiation, vasospasm, neurodegenerative disease, neurodegenerative process, infection, epilepsy & their secondary effects.

Neuroprotective is defined herein as an effect which reduces, arrests, or ameliorates nervous insult & is protective, resuscitative or revivative for nervous tissue that has suffered nervous insult.

Neuroprotective agent is herein defined as treatment medication, or formulary drug containing a nervous insult treatment dose of treatment medication effective in reducing, arresting, or ameliorating nervous insult & provides protection, resuscitation or revival to nervous tissue that has suffered nervous insult.

The present invention is that cyclosporins are neuroprotective agents.

The present invention is also that treatment medications containing a nervous insult treatment dose of cyclosporins are neuroprotective agents.

The present invention is further that formulary drugs, as below defined, containing a nervous insult treatment dose of treatment medications are neuroprotective agents.

Cyclosporins are neuroprotective by the mechanism of protecting the intracellular biochemistry, form, function & organelles from irreversible damage during the period of loss of cellular homeostasis. The pathway from cell damage to cell death is blocked by this neuroprotective agent, so that once the physiologic disruption passes, the cell is able to re-establish equilibrium & repair the damage, instead of dying. No treatment medication blocks the nervous tissue cell death as well as cyclosporins. Cyclosporins blocks either the final common pathway to cell death, or blocks several crucial sequential steps, or parallel biochemical & organelle failure pathways leading to cell death. This powerful cerebral neuroprotective action has not hitherto been disclosed from any of the known cerebral therapeutic medications from the state of the art.

The present invention is a novel & completely new application for the cyclosporins. Cyclosporins, as cyclic peptides, are a completely new class of substances than those before found useful as neuroprotective. Cyclosporins are neuroprotective agents for treating cerebral disturbances & insufficiencies of various origins. Cyclosporins are neuroprotective agents at acceptable physiologic & pharmacologic doses. Cyclosporins are particularly suited for treating nervous insults from cerebral vascular diseases & insufficiencies, hypoxias & traumatic brain damage. The invention is for the general neuroprotective effect of cyclosporins, in all conditions compromising the cellular viability of nervous tissue.

The invention is the use of cyclosporins for obtaining a treatment medicine and formulary drug intended for the therapeutic neuroprotective use of treating the following conditions, situations & diseases in which nervous insult occur: Trauma (such as penetrating injury, closed head injury, intracranial mass & raised intracranial pressure, surgery & iatrogenic damage), physiologic abnormalities (such as electrolyte, glucose, vitamin, metabolic, homeostatic), poisons (such as metabolic, toxins, neurotoxins), radiation ( including acute & delayed effects) & vasospasm & for each of the above, their secondary & delayed effects: To special systems including visual & optic, auditory, vestibular, & olfactory: To regions of special interest in addition to the brain including nervous tissues of the brain stem, spinal cord (such as myelitis & myelopathy), & the peripheral nervous system: From the diseases & processes of neurodegeneration (such as Alzheimer's, Parkinson's, Huntington's etc.), epilepsy ( including status epilepticus), infection (such as herpes infection, AIDS related neurological sequelae, AIDS myelopathy, etc.) & ageing.

Cyclosporins are suited for the neuroprotective treatment of nervous insult to embryonic & fetal nervous tissue for cell culture, production, & clinical transplantation therapies in humans.

Cyclosporins are suited for the neuroprotective treatment of neural cell cultures, glial cell cultures, neural & glial cell cultures, both neural & glial origin tumor cell cultures, tranfected, genetically engineered cell cultures, including those of peripheral origin such as sympathetic ganglia, dorsal root ganglia, pheochromocytomas & Schwann cells.

The invention is the use of cyclosporins for obtaining a treatment medication and formulary drug intended for the therapeutic neuroprotective use of treating the following conditions, situations & diseases in which nervous insult occur: from cerebrovascular accidents, stroke & ischemic damage. Causes & sources of cerebrovascular accident include intracranial sources, pressure related ischemia, extracranial sources, embolic sources, vasculopathy, & coagulopathy. Causes & sources of hypoxia include respiratory compromise & full body hypoxia, anemia, red blood cell & hemoglobin malfunction, & hypotension.

This patent application is for the administration of cyclosporins both before, or during & after a nervous insult has occurred as neuroprotection for nervous tissue & nervous function. This is a new treatment of nervous insult.

The neuroprotective properties of cyclosporins were previously unknown because cyclosporins do not normally cross the blood-brain barrier. This invention is that cyclosporins are neuroprotective in conditions, situations & methods wherein the blood-brain barrier has been opened, disrupted, bypassed, transgressed, obviated or crossed so that cyclosporins can come into contact with nervous tissue.

The blood-brain barrier is present in the endothelial cells lining the capillaries of the brain. Between these special endothelial cells are close knit connections called zonulae occludentes which prevent the diffusion of larger molecules from the vascular space into the brain. There is an electrostatic charge on the vascular surface of the capillaries, which repels charged molecules & blocks their entry. There is a mechanism of active transport of certain molecules into the brain, & others out. Highly lipid soluble drugs usually cross the blood-brain barrier easily. Methods for breaching this barrier are well known in the art, & include administration of hypertonic solutions intra-arterially & intravenously, administration of charged chemicals, mechanical disruption, trauma, packaging the treatment medication within microsomes, altering the treatment medication to make it more lipophilic or conjugating it to another substance which crosses easily.

The same principles apply to other methods of delivery. Specifically in the case of intra-arterial injection, with catheter injection or infusion into cerebral artery leading to the brain, the agent to open the blood-brain barrier & treatment medications might be administered one after the other, or together. Cyclosporins could be administered via venous route, while the drug to open the blood-brain barrier could be administered by arterial route.

Experimental animals were subjected to hypotension by exsanguination, and forebrain ischemia by clamping the bilateral carotid arteries for 10 minutes. The neurons of the CA1 area of the hippocampus are highly sensitive to ischemic insult, with their resultant cell death. Animals that received vehicle with or without opening the blood-brain barrier had more than 80% cell death. Animals that received cyclosporin A but without opening the blood-brain barrier had more than 80% cell death. Animals that received cyclosporin A with the opening of the blood-brain barrier had only 11% cell death. This dramatic neuroprotection is much greater than for any other known neuroprotective agent. This neuroprotection from hypoxic and ischemic insult by a combination of cyclosporin & opening the blood-brain barrier is a novel discovery.

Normally cyclosporins are unable to cross the blood-brain barrier. While they are lipophilic substances, they are thought to be blocked by the endothelial cell tight junctions. Interestingly, once the blood-brain barrier is disrupted, such as in culture, cyclosporins are specifically taken up & accumulated in neurons, achieving a high neuron to solution ratio of 20 after 25 minutes. This suggests, that if the blood-brain barrier where opened for even a short time, significant quantities could be actively taken into the brain neurons. Once the blood-brain barrier reclosed, the cyclosporins would remain trapped in the brain. The endothelial cells of the brain capillaries also have an ATP dependent active efflux mechanism for cyclosporins on their luminal surface mediated by the "multidrug transporter" P-glycoprotein. If cyclosporins were able to enter the endothelial cells, then their lipophilic nature would probably allow them ready access to the adjoining glia & neurons. Short term blocking or "poisoning" of this P-glycoprotein with medications or antibodies might provide an elegant & simple entry of cyclosporins across the blood-brain barrier during the crucial early hours after ischemia.

Cyclosporins can cross the blood-brain barrier in a number of ways: After cerebrovascular accident, the ischemia itself disrupts the blood-brain barrier within 6 hours, & molecules such as cyclosporins are able to enter the brain: Osmotic agents such as hypertonic radiocontrast agents, mannitol, urea, arabinose & saccharose solutions are able to temporarily disrupt the blood-brain barrier which can allow therapeutic drug delivery to the brain. These are typically given as hypertonic solution infused for 30 seconds through a major cerebral artery. The increased permeability can begin immediately & lasts between 20 minutes to 2 hours, with blockage of large molecules before small ones. This method of opening the blood-brain barrier for delivery of otherwise excluded chemotherapeutic drugs is used successfully to treat brain tumours in humans: The blood-brain barrier could be opened by the less invasive & more convenient intravenous route (through standard intravenous line in the antebrachial vein of the arm) with a mannitol solution: Chemicals such as positively charged protamine, disrupt the negative repulsing charge on the brain vascular endothelium, temporarily opening the blood-brain barrier. These are typically given by intracarotid injection: Cyclosporins could be altered in their composition chemically to better cross the blood-brain barrier by making it more lipid soluble, by (de)glycosylating, by cationizing, by liposome entrapping or by coupling or conjugating with a substance or carrier that facilitates transfer across the blood-brain barrier.

Administration of the treatment medication may be by any suitable route including oral, sublingual, buccal, nasal, inhalation, parenteral (including intraperitoneal, intraorgan, subcutaneous, intradermal, intramuscular, intra-articular, venous (central, hepatic or peripheral), lymphatic, cardiac, arterial, including selective or superselective cerebral arterial approach, retrograde perfusion through cerebral venous system, via catheter into the brain parenchyma or ventricles), direct exposure or under pressure onto or through the brain or spinal tissue, or any of the cerebrospinal fluid ventricles, injections into the subarachnoid, brain cisternal, subdural or epidural spaces, via brain cisterns or lumbar puncture, intra & peri-ocular instillation including application by injection around the eye, within the eyeball, its structures & layers, the ear, including the Eustachian tube, mastoid air cells, external & internal auditory canals, tympanic membrane, middle ear, inner ear including the cochlear spiral ganglion & labyrinthine organs, as well as via enteral, bowel, rectal, vaginal, urethral or bladder cisternal. Also for in utero & perinatal indications then injections into the maternal vasculature, or through or into maternal organs including the uterus, cervix & vagina, & into embryo, fetus, neonate & allied tissues & spaces such as the amniotic sac, the umbilical cord, the umbilical artery or veins & the placenta, with parenteral being the preferred route. The preferred route may vary depending on the condition of the patient.

Included in the invention is administration of the treatment medication via any means with purposeful disruption of brain or spinal parenchyma, or disrupting the blood-brain barrier via mechanical, thermal, cryogenic, chemical, toxic, receptor inhibitor or augmentor, osmotic, charge altering, radiation, photon, electrical or other energy or process.

This invention includes all methods of administering treatment medications along with all methods of opening, bypassing or disrupting the blood-brain barrier in combination, simultaneously or in sequence to get the treatment medication in contact with nervous tissues.

This invention includes the possibility of the timing & sequence of delivery of treatment medications to include pretreatment; For the treatment medications to have the best opportunity to protect nervous tissue from nervous insult, it needs to be available as soon as possible within the affected cells. This would include administration before the nervous ischemic insult in situations of increased likelihood of ischemia or stroke. Known or anticipatory situations include surgery (carotid endarterectomy, cardiac, vascular, aortic, orthopedic), endovascular procedures such as any type of arterial catheterization (carotid, vertebral, aortic, cardiac, renal, spinal, Adamkiewicz & others) for diagnostic or therapeutic purposes including evaluation & treatment of vascular stenosis, aneurysm or arteriovenous malformation &/or injection of embolic agents, coils or balloons for hemostasis, interruption of vascularity or treatment of brain lesions, predisposing medical conditions, including crescendo transient ischemic attacks, anticipated emboli or sequential strokes: Post-treatment; For stroke, or ischemia that has occurred prior to the administration of cyclosporins, it is important to get the drug to the affected cells as quickly as possible during or after the event. The time between stroke, diagnosis & treatment should be reduced to its minimum to save the ischemic cells from damage & death. The ideal temporal relation would be the simultaneous opening of the blood-brain barrier & availability of cyclosporins to enter the brain & ischemic tissue as soon after the stroke as possible.

While it is possible to administer the treatment medication to be administered alone, it is preferred to present it as part of a pharmaceutical formulary drug. The formulary drug of this invention comprise at least one administered treatment medication as defined above together with one or several appropriate carriers thereof & possibly other pharmaceutical treatment medications. The carriers must be appropriate in that they can readily coexist with the other agents of the formulary drug & are not detrimental to the receiver thereof. This treatment medication combined, as described in this paragraph, with other appropriate agents common to the art, is defined herein as the formulary drug.

The formulary drug includes those suitable for administration by the routes including oral, sublingual, buccal, nasal, inhalation, parenteral (including intraperitoneal, intraorgan, subcutaneous, intradermal, intramuscular, intra-articular, venous (central, hepatic or peripheral), lymphatic, cardiac, arterial, including selective or superselective cerebral arterial approach, retrograde perfusion through cerebral venous system, via catheter into the brain parenchyma or ventricles), direct exposure or under pressure onto or through the brain or spinal tissue, or any of the cerebrospinal fluid ventricles, injections into the subarachnoid, brain cisternal, subdural or epidural spaces, via brain cisterns or lumbar puncture, intra & peri-ocular instillation including application by injection around the eye, within the eyeball, its structures & layers, the ear, including the Eustachian tube, mastoid air cells, external & internal auditory canals, tympanic membrane, middle ear, inner ear including the cochlear spiral ganglion & labyrinthine organs, as well as via enteral, bowel, rectal, vaginal, urethral or bladder cisternal. Also for in utero & perinatal indications then injections into the maternal vasculature, or through or into maternal organs including the uterus, cervix & vagina, & into embryo, fetus, neonate & allied tissues & spaces such as the amniotic sac, the umbilical cord, the umbilical artery or veins & the placenta, with parenteral being the preferred route.

The formulary drug may be distributed and made available in convenient unit dose form such as capsules & ampoules, containing the treatment medication of the invention, & may be manufactured & distributed by any of the methods known to the pharmaceutical arts. In addition to the treatment medication, the formulary drug can also contain other usual agents of the art relating to the type of formulary drug produced. The formulary drug may, by example, take the configuration of suspensions, solutions & emulsions of the treatment medication in lipid, non-aqueous or aqueous diluents, solvents, dissolving agents, emulsifiers, syrups, granulates or powders, or mixtures of these. The formulary drug can also contain coloring agents, preservatives, perfumes, flavoring additions & sweetening agents. In addition to the treatment medication, the formulary drug can also contain other pharmaceutically active medications. The manufacture and distribution of the formulary drug is carried out by techniques known to the art, such as, evenly & intimately bringing together the treatment medication with liquids or fine solids or both, & then if needed, forming the formulary drug into a dose unit form. The discrete dose, portion & carrier vehicle constituting the formulary drug will generally be adapted by virtue of shape or packaging for medical administration and distributed for this purpose.

The formulary drug acceptable for oral administration may be manufactued and distributed as individual dosage units such as capsules, pills, tablets, dragees, dissolvable powders, or cachets, each containing a known dose of the treatment medication; as powder or granules; as solution or suspension in syrups, elixirs as a lipid, aqueous liquid or a non-aqueous liquid; or as an oil-in-water emulsion or as a water-in-oil emulsion.

Tablets can be manufactured & distributed by compression or mould, from treatment medication possibly with one or more additional pharmaceutically active compounds. Compressed tablets can be manufactured & distributed through compression in a machine typical to the art a known quantity of the treatment medication in a dispersible configuration such as powder or granules, possibly mixed with other agents including binders, lubricants, inert diluents, preservatives, & dispersing agents. Moulded tablets can be manufactured & distributed by moulding in a machine typical to the art a mix of known quantity of treatment medication addition pharmaceutically active compounds & other additives moistened with a liquid diluent. The tablets can possibly be coated, enveloped or covered, with substances including protective matrices, which can contain opacifiers or sweeteners & can be formulated to allow slow or controlled release, or also release within a certain part of the digestive system of the contained treatment medications. Capsules can be manufactured & distributed by placement of a known quantity of treatment medication, additional pharmaceutically active compounds & additives within a two part or sealed capsule of gelatine or other aqueous dissolvable substance. The treatment medication can also be manufactured & distributed as formulary drug in microencapsulated, microsomal, micellar and microemulsion forms.

The formulary drug containing the treatment medication acceptable for oral topical administration can be manufactured & distributed as lozenges containing the treatment medications, other pharmaceutically active compounds, & additives in a flavored basis, such as acacia & tragacanth; Pastilles containing the active treatment medication with other pharmaceutically active compounds, & additives in an inert base such as gelatine & sucrose: Mouthwashes or rinses containing the treatment medication with other pharmaceutically active compounds, & additives in an acceptable liquid.

The formulary drug containing the treatment medication acceptable for skin topical administration can be manufactured & distributed as ointments, oils, creams, lotions, gels, pastes & transdermal patch containing the treatment medication, other pharmaceutically active compounds, additives & an acceptable carrier medium.

The formulary drug containing the treatment medication acceptable for nasal administration can be manufactured & distributed with other pharmaceutically active compounds & additives as a powder for inhalation, or as an oily, aqueous or non-aqueous liquid for nasal spray or drops.

The formulary drug containing the treatment medication acceptable for rectal administration can be manufactured & distributed as suppositories, creams, foams, douches or enemas with other pharmaceutically active compounds, suitable bases of the usual water-soluble diluents, fats, & additives known to practitioners of the art.

The formulary drug containing the treatment medication acceptable for vaginal administration can be manufactured & distributed as pessaries, suppositories, creams, gels, foams, douches or sprays with other pharmaceutically active compounds, suitable bases & additives known to practitioners of the art.

The formulary drug containing the treatment medication acceptable for parenteral administration can be manufactured & distributed from aqueous & non-aqueous sterile injection solutions, other pharmaceutically active compounds, additives including anti-oxidants, bacteriostats & solutes & sugars such as mannitol to make the formulary drug isotonic, hypotonic or hypertonic with the blood of the recipient; & also aqueous & non-aqueous sterile suspensions which can include suspenders & thickeners. The formulary drug can be manufactured & distributed in unit-dose or multi-dose containers, such as sealed glass or plastic ampoules, vials, bottles & bags as a liquid, & in a dry state requiring only the addition of sterile liquid, for example water, saline or dextrose solutions, immediately prior to use. Extemporaneous solutions & suspensions for injection can be prepared from powders & tablets of the kind above described.

The formulary drug containing the treatment medication acceptable for administration into the brain & related structures, spinal cord & related structures, ventricular system & cerebrospinal fluid spaces can be manufactured & distributed from aqueous & non-aqueous sterile injection solutions, other pharmaceutically active compounds, additives including anti-oxidants, bacteriostats & solutes & sugars such as mannitol to make the formulary drug isotonic, hypotonic or hypertonic with the cerebrospinal fluid; & also aqueous & non-aqueous sterile suspensions which can include suspenders & thickeners. The formulary drug can be manufactured & distributed in unit-dose or multi-dose containers, such as sealed glass or plastic ampoules, vials, bottles & bags as a liquid, & in a dry state requiring only the addition of sterile liquid, for example water, saline or dextrose solutions, immediately prior to use. Extemporaneous solutions & suspensions for injection can be prepared from powders & tablets of the kind above described.

The desired unit dose of formulary drug are those containing a daily dose or nervous insult treatment dose or an appropriate fraction thereof, of the administered treatment medication. Unit dose forms of the invention may also include more complex systems such as double barrelled syringes, syringes with sequential compartments one of which may contain the treatment medication, & the other any necessary diluents or vehicles, or agents for opening the blood-brain barrier. The agents in the syringes would be released sequentially or as a mixture or combination of the two after the triggering of the syringe plunger. Such systems are known in the art.

The formulary drug generally contains from 0.1 to 90% of the treatment medication by weight of the total composition. Amounts of from 0.0001 mg to 50 mg/kg, or preferably 0.001 to 25 mg/kg, of body weight per day for parenteral administration & 0.001 to 100 mg/kg, preferably 0.01 to 60 mg/kg, of body weight per day for enteral administration, can be given to achieve neuroprotection. Nevertheless, it could be necessary to alter those dosage rates, depending on the condition, weight, and individual reaction of the subject to the treatment, the type of formulary drug in which the treatment medication is administered & the mode in which the administration is carried out, & the stage of the disease process or interval of administration. It may thus be sometimes adequate to use less than the before stated minimum dose, while in other instances the upper limit must be surpassed to obtain therapeutic results.

The invention is for the use of the treatment medication in the conditions described throughout the application. The invention thus also includes all advertising, labelling, packaging, informational materials, inserts, product descriptions, advertising materials, the written word, including letter, pamphlet, brochures, magazines & books, as well as other medium of communication including the spoken word, fax, phone, photos, radio, video, television, film, internet, e-mail or computer based, & proposals for clinical trials and study protocols for clinical trials using the treatment medication for its neuroprotective effect.

The following Examples 1 through 10 illustrate the invention.

Examples 1 through 6 illustrate conditions & situations wherein can be gotten, & which are means to getting, the treatment medication of the invention in contact with nervous tissue, that is, when the blood brain barrier is disrupted or open.

EXAMPLE 1

Under local anesthesia, a catheter is inserted percutaneously in the femoral artery & then passed cephalad into one of the internal carotid arteries. A volume of 270 ml of hypertonic solution of 20% mannitol is infused at a rate of 9 ml per second for 30 seconds into the internal carotid artery to produce blood-brain barrier disruption & opening. The extent of blood-brain barrier opening can be seen with MRI or contrast CAT scan.

EXAMPLE 2

Under local anesthesia & sedation, incision is made through the scalp, exposing the bone of the skull. A drill is used to make a hole through the skull. The dura is opened. A catheter is placed through the brain parenchyma, disrupting & opening the blood-brain barrier. The catheter tip will rest within the ventricular system.

EXAMPLE 3

A patient has had a cerebrovascular accident with breakdown & opening of the blood-brain barrier.

EXAMPLE 4

A patient has had trauma to the head, with disruption of brain tissue & disruption & opening of the blood-brain barrier.

EXAMPLE 5

A patient has had trauma to the spinal cord, with disruption of spinal cord tissue & disruption & opening of the blood-brain barrier in the spinal cord.

EXAMPLE 6

A patient has had surgery of the brain, with disruption & opening of the blood-brain barrier.

Once the blood-brain barrier is disrupted or opened, the following examples 7 through 10 illustrate to be administered formulary drugs of the invention.

EXAMPLE 7

| Sterile Injectable Concentrate Formulary Drug | |
|---|---|
| Containing per ml: | |
| Cyclosporin A | 50 mg |
| Spiritus fortis | 280 mg |
| Polyoxyethylated castor oil | 650 mg |

The formulary drug is sterilized by heat or radiation & then placed in a sealed container such as glass in doses of 1 or 5 ml.

Sterile injectable concentrate formulary drug is diluted 1 ml in 20 ml saline so that it may be administered by infusion or by injection into artery, vein, brain, spine or cerebrospinal fluid spaces.

EXAMPLE 8

| Capsule Formulary Drug | |
| --- | --- |
| Cyclosporin A | 100 mg |
| Iron oxide E172 | 1 mg |
| Titanium dioxide | 3 mg |
| Ethanol | 100 mg |
| Corn oil | 415 mg |
| Gelatine | 280 mg |
| Labrafil | 300 mg |
| Andrisorb | 105 mg |
| Glycerol 85% | 3 mg |

A one or two part capsule is prepared by placing the formulary drug in a one or two part gelatine capsule.

EXAMPLE 9

| Capsule Enhanced Absorption Formulary Drug | |
| --- | --- |
| Cyclosporin A | 100 mg |
| Iron oxide E172 | 1 mg |
| Titanium dioxide | 2 mg |
| Propylene glycol | 150 mg |
| Tocopherol | 1 mg |
| Ethanol | 100 mg |
| Corn oil | 345 mg |
| Gelatine | 300 mg |
| Glycerol 85% | 40 mg |
| Polyoxyl 40 hydrogenated castor oil | 405 mg |

A one or two part capsule is prepared by placing the formulary drug in a one or two part gelatine capsule.

EXAMPLE 10

| Liquid Oral Formulary Drug | |
| --- | --- |
| Containing per 1 ml: | |
| Cyclosporin A | 100 mg |
| Ethanol | 100 mg |
| Corn oil | 430 mg |
| Labrafil | 300 mg |

What is claimed is:

1. A method of treating a human with nervous insult, with the exclusion of nervous ischemic insult, comprising the administration of an effective nervous insult treatment amount of cyclosporin A to said human in whom the blood-brain barrier has been opened, or where cyclosporin A is able to cross the blood-brain barrier.

2. A method of treating a human with nervous insult, with the exclusion of nervous ischemic insult, comprising the administration of an effective nervous insult treatment amount of cyclosporins, or functional derivatives, metabolites, variants or salts thereof, to said human in whom the blood-brain barrier has been opened, or where cyclosporins are able to cross the blood-brain barrier.

3. The method of claim 1 or claim 2 in which the treatment medication containing cyclosporin A or cyclosporins is administered orally.

4. The method of claim 1 or claim 2 in which the treatment medication containing cyclosporin A or cyclosporins is administered intra-arterially or intra-venously as a sterile injectable formulary drug.

5. The method of claim 1 or claim 2 in which the treatment medication containing cyclosporin A or cyclosporins is administered parenterally as a sterile injectable formulary drug.

6. The method of claim 1 or claim 2 in which the treatment medication containing cyclosporin A or cyclosporins is administered into or adjacent to the brain, cerebrospinal fluids or spinal cord as a sterile injectable formulary drug.

7. The method of claim 1 or claim 2 in which the treatment medication containing cyclosporin A or cyclosporins is administered by a combination of the routes of method of claim 3, claim 4, claim 5, or claim 6.

8. A method of treating a human with nervous ischemic insult comprising the administration of an effective nervous ischemic insult treatment amount of cyclosporin A to said human in whom the blood-brain barrier has been opened or where cyclosporin A is able to cross the blood-brain barrier.

9. A method of treating a human with nervous ischemic insult comprising the administration of an effective nervous ischemic insult treatment amount of cyclosporins, or functional derivatives, metabolites, variants or salts thereof, to said human in whom the blood-brain barrier has been opened, or where cyclosporins are able to cross the blood-brain barrier.

10. The method of claim 8 or claim 9 in which the treatment medication containing cyclosporin A or cyclosporins is administered orally.

11. The method of claim 8 or claim 9 in which the treatment medication containing cyclosporin A or cyclosporins is administered intra-arterially or intravenously as a sterile injectable formulary drug.

12. The method of claim 8 or claim 9 in which the treatment medication containing cyclosporin A or cyclosporin is administered parenterally as a sterile injectable formulary drug.

13. The method of claim 8 or claim 9 in which the treatment medication containing cyclosporin A or cyclosporins is administered into or adjacent to the brain, cerebrospinal fluids or spinal cord as a sterile injectable formulary drug.

14. The method of claim 8 or claim 9 in which the treatment medication containing cyclosporin A or cyclosporins is administered by a combination of the method of claim 10, claim 11, claim 12, or claim 13.

15. An article of manufacture comprising packaging material and pharmaceutical agent contained within said packaging material, wherein the pharmaceutical agent is therapeutically effective for reducing or preventing nervous damage caused by traumatic, metabolic, ischemic or hypoxic neural insult when the pharmaceutical agent is able to cross the blood-brain-barrier to contact the nervous tissue in a therapeutically effective quantity, and wherein the packaging material comprises a label which indicates that the pharmaceutical agent can be used for reducing or preventing nervous damage caused by traumatic, metabolic, ischemic or hypoxic neural insult, and wherein said pharmaceutical agent comprises cyclosporin A or a compound of the class of cyclosporins, or functional derivatives, metabolites, variants or salts thereof, or combination of the before said, either alone or in admixture with diluents, or additives.

16. An article of manufacture comprising packaging material and two pharmaceutical agents contained within said packaging material, wherein the first pharmaceutical agent is therapeutically effective for reducing or preventing nervous damage caused by traumatic, metabolic, ischemic or hypoxic neural insult when the first pharmaceutical agent is able to cross the blood-brain-barrier to contact the nervous tissue in a therapeutically effective quantity, and wherein the second pharmaceutical agent increases the permeability of the blood-brain-barrier to the first pharmaceutical agent, and wherein the packaging material comprises a label which indicates that the two pharmaceutical agents can be used together for reducing or preventing nervous damage caused by traumatic, metabolic, ischemic or hypoxic neural insult, and wherein said first pharmaceutical agent comprises cyclosporin A or a compound of the class of cyclosporins, or functional derivatives, metabolites, variants or salts thereof, or combination of the before said, either alone or in admixture with diluents, or additives, and wherein said second pharmaceutical agent comprises one or several compounds that open the blood-brain-barrier through one or several mechanisms including hyperosmotic mannitol solution, protamine sulfate electrostatic charge blocker, and inhibitors of the P-glycoprotein muitidrug transporter system either alone or in admixture with diluents, or additives.

* * * * *